(12) United States Patent
Reedy et al.

(10) Patent No.: US 6,518,335 B2
(45) Date of Patent: *Feb. 11, 2003

(54) SULFUR-CONTAINING SILANE COUPLING AGENTS

(75) Inventors: James D. Reedy, Belpre, OH (US); Kenneth W. Hartman, Middlebourne, WV (US)

(73) Assignee: Crompton Corporation, Middlebury, CT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 184 days.

(21) Appl. No.: 09/478,283

(22) Filed: Jan. 5, 2000

(65) Prior Publication Data

US 2002/0002220 A1 Jan. 3, 2002

(51) Int. Cl.$^7$ .................................................. C07F 7/08
(52) U.S. Cl. ................... 524/82; 556/429; 556/479; 556/427; 524/84; 524/188; 524/262
(58) Field of Search ................. 556/427, 429; 568/590; 524/82, 84, 188, 262; 526/917

(56) References Cited

U.S. PATENT DOCUMENTS

| | | | |
|---|---|---|---|
| 3,451,458 A | 6/1969 | Stueber | 152/330 |
| 3,842,111 A | 10/1974 | Meyer-Simon et al. | 260/448.2 |
| 3,873,489 A | 3/1975 | Thurn et al. | 260/33.6 |
| 3,946,059 A | 3/1976 | Janssen et al. | 260/448.2 |
| 3,978,103 A | 8/1976 | Meyer-Simon et al. | 260/448.8 |
| 3,997,581 A | 12/1976 | Pletka et al. | 260/448.8 |
| 4,072,701 A | 2/1978 | Pletka et al. | 260/448.8 |
| 4,129,585 A | 12/1978 | Buder et al. | 260/448.8 |
| 4,384,132 A | 5/1983 | Schwarz et al. | 556/427 |
| 4,408,064 A | 10/1983 | Schwarz et al. | 556/427 |
| 4,444,936 A | 4/1984 | Schwarz et al. | 524/393 |
| 4,507,490 A | 3/1985 | Panster et al. | 556/427 |
| 4,704,414 A | 11/1987 | Kerner et al. | 523/213 |
| 4,968,560 A | * 11/1990 | Lechner et al. | |
| 5,110,969 A | 5/1992 | Dittrich et al. | 556/427 |
| 5,227,425 A | 7/1993 | Rauline | 524/493 |
| 5,286,815 A | 2/1994 | Leir et al. | |
| 5,405,985 A | 4/1995 | Parker et al. | 556/427 |
| 5,468,893 A | 11/1995 | Parker et al. | 556/427 |
| 5,674,932 A | 10/1997 | Agostini et al. | 524/430 |
| 5,675,014 A | * 10/1997 | Cohen et al. | |
| 5,753,732 A | 5/1998 | Wideman et al. | 524/263 |
| 5,892,085 A | * 4/1999 | Munzenberg et al. | |
| 5,916,973 A | 6/1999 | Zimmer et al. | |
| 6,005,027 A | * 12/1999 | Guillet et al. | |
| 6,147,241 A | * 11/2000 | Michel et al. | |
| 6,153,782 A | * 11/2000 | Krauter et al. | |
| 6,218,561 B1 | * 4/2001 | Wideman et al. | |

FOREIGN PATENT DOCUMENTS

| | | |
|---|---|---|
| DE | 197 02 046 | 1/1998 |
| EP | 0 217 178 A2 | 4/1987 |
| EP | 0 507 727 A2 | 10/1992 |
| EP | 0 773 224 A2 | 5/1997 |
| EP | 0 732 362 B1 | 6/1999 |
| EP | 0 963 995 A2 | 12/1999 |
| EP | 1 035 162 A2 | 9/2000 |
| JP | 09176323 | 8/1997 |
| JP | 09316330 | 9/1997 |
| WO | 9909036 | 2/1999 |
| WO | WO 99/15583 | 4/1999 |

OTHER PUBLICATIONS

Buder, Wolfgang; "Synthesis and Spectroscopic study of trimethoxysilylproplysulfanes", Anorg. Chem., Org. Chem., vol 34B, 6, p 790–793 (1979).

Perard, et al.; "18–Functionalized steriods: synthesis of thio derivatives of Progesterone" Steroids, vol. 55, 6, p 271–275 (1990).

esp@net abstract for DE 19702046 (abstracting EP 0819694).

esp@net abstract for EP 0773224 (abstracting US 5663395).

* cited by examiner

*Primary Examiner*—Robert Dawson
*Assistant Examiner*—Marc S. Zimmer
(74) *Attorney, Agent, or Firm*—Michael P. Dilworth

(57) ABSTRACT

A method is provided for preparing sulfur-containing silane coupling agents by reacting an alkoxysilane acetal with a sulfurating agent. The sulfur-containing silane coupling agents so prepared include certain novel mercapto silanes, and are useful in providing rubber tires with improved properties.

15 Claims, No Drawings

SULFUR-CONTAINING SILANE COUPLING AGENTS

BACKGROUND OF THE INVENTION

Sulfur-containing silane coupling agents are useful in providing rubber, including automotive tires, with improved properties, generally by coupling inorganic fillers or fibers with the rubber matrix in a fashion which leads to the improved properties. The sulfur-containing silane coupling agents which have achieved commercial success to date have been produced by disadvantageous processes which involve the handling of large quantities of chlorine-containing by-products. Thus, there is an ongoing need in the art to prepare sulfur-containing silane coupling agents safely in high yields and efficiencies by processes which do not involve chlorine-containing intermediates or by-products.

Current large-scale commercial production of such sulfur-containing silane coupling agents is based on the raw material trichlorosilane. Trichlorosilane is reacted with either allyl chloride or vinyltoluene to provide the respective intermediates, 3-chloropropyltrichlorosilane or (trichlorosilylethyl)-toluene. The former is reacted with alcohol to produce a 3-chloropropyltrialkoxysilane, which is reacted with sodium hydrosulfide or sodium tetrasulfide to produce the desired products, plus four equivalents of chlorine. The latter is reacted with sulfur monochloride, and the sulfurated trichlorosilane intermediate is reacted with alcohol to produce the desired product, plus five equivalents of chlorine.

Both of the above embodiments suffer from additional disadvantages in that yields from the reaction of trichlorosilane with allyl chloride are well below quantitative, based on the limiting reactant, with concurrent generation of undesired by-products. The reaction of trichlorosilane with vinyltoluene is susceptible to polymerization of the vinyltoluene, with subsequent reduced efficiency to (trichlorosilylethyl) toluene and formation of a polymeric by-product.

There is a need for a process that can simply and efficiently prepare certain known and novel silane coupling agents by a direct reaction, not producing chlorine-containing by-products. More specifically, there is a need for a process to produce sulfur-containing coupling agents that does not begin with trichlorosilane and does not involve chlorine-containing intermediates or by-products.

SUMMARY OF THE INVENTION

The present invention provides a process for preparing sulfur-containing silane coupling agents, some of which are novel compositions, by the reactions of alkoxysilane acetals with nonionic, chlorine-free sulfurating agents including, but not limited to, thiols, di- and higher thiols, hydrogen sulfide, and sulfur, in the presence of an acid catalyst, and optionally in the presence of hydrogen and a reduction catalyst. The process is depicted by the general reaction:

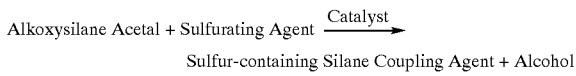

DETAILED DESCRIPTION OF THE INVENTION

It is an object of the invention to provide an improved process for the synthesis of sulfur-containing silane compounds, useful as coupling agents, by reactions involving chlorine-free intermediates and sulfurating agents. It is another object of the invention to provide novel sulfur-containing silane compounds, useful as coupling agents. It is another object of the invention to provide a process for preparing intermediates for sulfur-containing silane compounds in high yields. It is yet another specific object of the invention to provide a process for preparing sulfur-containing silane compounds by a chlorine-free reaction that produces silanes without the production of undesired chlorine or polymeric intermediates or by-products.

It has been discovered that the acetal groups of alkoxysilane acetals can be reacted with sulfurating agents without causing significantly adverse reactions at the alkoxysilane groups. More particularly, the process of the invention is based on the following reaction:

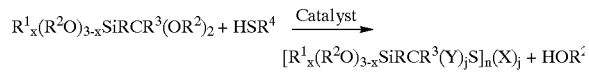

where R is a saturated or unsaturated linear, branched, or cyclic divalent hydrocarbon group of 2 to 12 carbon atoms optionally containing divalent —O— or —S— linkages; $R^1$ is an alkyl group of 1 to 4 carbon atoms, an aryl group of 6 to 12 carbon atoms, or an aralkyl or alkaryl group of 7 to 13 carbon atoms; each $R^2$ can be $R^1$ or the 2 $R^2$ groups taken together form an R group so as to form a ring; $R^3$ is a hydrogen atom or $R^1$; $R^4$ is $R^3$, —RSH, or —RSiR$^1_x$(OR$^2$)$_{3-x}$; x is an integer having a value of 0, 1, or 2, j=0 or 1, n is an integer having a value of 1 to 4; when n=1, j=1, when n>1, j=0, X is $R^4$ and Y is —SR$^4$ or —OR$^2$, or alternatively X and Y taken together are —SR— which forms a 1,3-dithiacycloalkane ring with the carbon bearing $R^3$, when n=1, or X and Y are both hydrogen atoms when n=1 and $R^4$ is a hydrogen atom. The sulfur-containing silane coupling agents provided by the process of the present invention may thus be monomers or oligomers and may contain more than one molecular species. Where more than one group of R, $R^1$, $R^2$, $R^3$, or $R^4$ is present in a molecule, said groups R, $R^1$, $R^2$, $R^3$, and $R^4$ may be the same or different.

The alkoxysilane acetal raw materials are well-known in the art. The normal preparation is by hydrosilation of an unsaturated acetal, $CH_2$=CR$^3$R$^5$CR$^3$(OR$^2$)$_2$, with a hydroalkoxysilane, $R^1_x(R^2O)_{3-x}SiH$, in the presence of a catalyst,

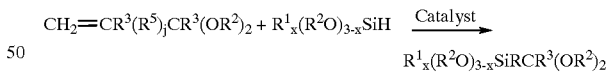

where j, R, $R^1$, $R^2$, and $R^3$ are as defined above; $R^5$ is a divalent saturated or unsaturated linear, branched, or cyclic hydrocarbon group of 1 to 10 carbon atoms, optionally containing —O— or —S— linkages; the divalent group R being formed from the group $CH_2$=CR$^3$R$^5$— upon hydrosilation.

The unsaturated acetals are articles of commerce, as are the hydroalkoxysilanes, and the catalysts used for hydrosilation. A particularly preferred hydroalkoxysilane is trimethoxysilane, as prepared by the direct reaction between silicon metal and methanol.

Preferred alkoxysilane acetal raw materials include compounds wherein R is a linear or branched divalent hydrocarbon group of 2 to 4 carbon atoms, $R^1$ is an alkyl group of 1 to 2 carbon atoms, $R^2$ is an alkyl group of 1 to 2 carbon atoms or 2 $R^2$ groups taken together form an R group, and $R^3$ is a hydrogen atom or an alkyl group of 1 to 2 carbon atoms. Most preferred versions of the alkoxysilane acetal include compounds wherein R is a linear divalent hydrocarbon group of 2 carbon atoms or a branched divalent hydrocarbon group of 3 carbon atoms, $R^1$ is a methyl group, $R^2$ is a methyl group or an ethyl group, and $R^3$ is a hydrogen or a methyl group. Thus, compounds in the most preferred group include the following:

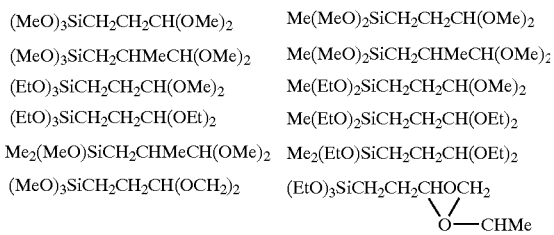

Preferred sulfurating agents will depend on the product desired and may be selected singly or in combination from the group of thiols, di- and higher thiols, hydrogen sulfide, and sulfur, optionally in the presence of hydrogen and an effective reduction catalyst. Sulfur serves as a source of hydrogen sulfide in the presence of hydrogen and an effective reduction catalyst. Dithiols, including 1,2-dimercaptoethane, 1,2-dimercaptopropane, and 1,3-dimercaptopropane are particularly preferred for preparing certain sulfur-containing silane coupling agents which are novel compositions. The ratio between silane and sulfurating agent is not narrowly critical, but preferably is between a slight excess of sulfurating agent to near stoichiometric equivalent.

A suitable reduction catalyst is selected from the group of metal-containing catalysts which are effective for reduction in the presence of sulfur and its compounds. Cobalt polysulfide is a preferred reduction catalyst for the process of the present invention, with a use level of 0.5 to 5 wt-% being preferred, and 1 to 3 wt-% being most preferred.

The process of the invention is preferably conducted in the presence of an acid catalyst, selected from the classes of protic (Bronsted) acids or nonprotic (Lewis) acids. The former is exemplified by para-toluenesulfonic acid and a wide variety of carboxylic and inorganic acids. The latter is exemplified by boron trifluoride, zinc salts, e.g., zinc chloride, and a number of other covalent metallic halides, including lanthanum chloride. Acids in solid or supported forms may also be used, including acid forms of zeolites, acid clays, sulfonated derivatives of fluoropolymers, and acids of either of the above classes deposited on inorganic supports. Selection of the acid catalyst is not a narrowly critical feature of the present invention, nor is its concentration. Any catalyst effective for the reaction can be used at an effective concentration. Acid concentrations in the range of 0.05 to 5 wt-% of the combined reactants are effective, with a concentration of 0.1 to 1 wt-% being preferred, and 0.1 to 0.5 wt-% being most preferred.

The process of the invention is performed at a temperature and pressure effective for the reaction, generally at an elevated temperature to assist in the removal of the alcohol by-product at ambient pressure. Preferred reaction temperatures are in the range of 40° to 200° C. and are not narrowly critical. The process may be run at atmospheric pressure for convenience, but may also be run at subatmospheric or superatmospheric pressures. Running at superatmospheric pressure will normally be necessary if a hydrogen atmosphere is maintained during the process in the presence of a reduction catalyst. Thus, equipment normally used for laboratory, pilot scale, or commercial scale synthetic chemistry, ranging form glassware to steel, may be used for the process of the present invention.

While the process of the present invention may be run in the absence of any solvent, solvents of various kinds may be used, for example, to assist in the introduction of raw materials and in the removal of the alcohol by-products. Among the available solvents are aromatic and aliphatic hydrocarbons, alcohols, ketones and ethers. Among the aromatic hydrocarbons are xylene, toluene, and benzene. Among the aliphatic hydrocarbons are pentane, hexane, heptane, octane, isooctane, decane, cyclohexane and methylcyclohexane. Among the alcohols are methanol, ethanol, isopropanol, propanol, butanol, hexanol, octanol and t-butanol. The ketones are represented by methyl ethyl ketone, methyl isopropyl ketone and cyclohexanone. The ethers are represented by tetrahydrofuran, dioxane, dioxolane and glyme. Certain of the solvents with low boiling points might require performing the reaction under elevated pressure.

Specific examples of products of the present invention may be selected, singly or in combinations, from the group of:

(Meo)$_3$Si(CH$_2$)$_3$SH; Me(MeO)$_2$Si(CH$_2$)$_3$SH; (EtO)$_3$Si(CH$_2$)$_3$SH; Me(EtO)$_2$Si(CH$_2$)$_3$SH; Me$_2$(Meo)Si(CH$_2$)$_3$SH; (Meo)$_3$SiCH$_2$CHMeCH$_2$SH; and Me(EtO)$_2$SiCH$_2$CHMeCH$_2$SH; which are known compositions of matter, and from the group of novel mercapto silane structures of:

$[R^1_x(R^2O)_{3-x}SiRC(R^3)(OR^2)S]_2R$;
$R^1_x(R^2O)_{3-x}SiRC(R^3)_2SRSH$;
$[R^1_x(R^2O)_{3-x}SiRCR^3S]q$ wherein $q \geq 2$, preferably 3; and
$R^1_x(R^2O)_{3-x}SiR\text{-cyclo}(C(R^3)SRS)$;

wherein $R^1$, $R^2$, $R^3$, R, and x are as above.

Examples of the foregoing novel structures are as follows:

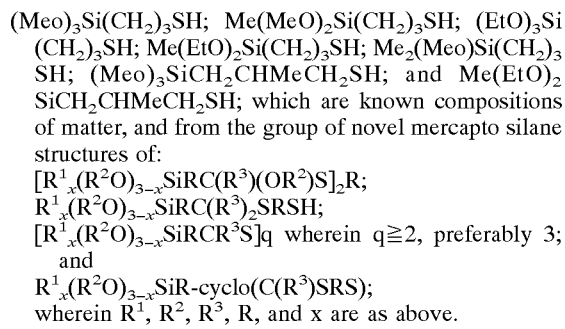

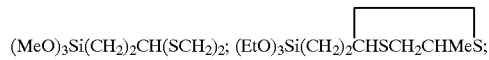

Me(MeO)$_2$Si(CH$_2$)$_2$CH(SCH$_2$)$_2$; (MeO)$_3$SiCH$_2$CHMeCH(SCH$_2$)$_2$;
(MeO)$_3$Si(CH$_2$)$_3$SCH=CHCH$_2$Si(OMe)$_3$;
(MeO)$_3$Si(CH$_2$)$_2$CH(OMe)S(CH$_2$)$_2$SH;[(MeO)$_3$Si(CH$_2$)$_2$CHS]$_3$;[Me(MeO)$_2$Si(CH$_2$)$_2$CHS]$_3$;
[MeO)$_3$Si(CH$_2$)$_2$CH(OMe)SCH$_2$]$_2$; [EtO)$_3$Si(CH$_2$)$_2$CHS]$_3$; and (MeO)$_3$Si(CH$_2$)$_3$S(CH$_2$)$_2$SH.

The reaction mixtures produced by the process of this invention will typically comprise a mixture of subject silanes and alcohol. Depending on the particular alcohol, transesterification with the alkoxy silane may occur. The alcohol may be removed by distillation or vacuum stripping. It is preferred to separate the alcohol to reduce its concentration to less than about 0.5%. There is typically no need to separate the individual silanes; however, where desired, this can be accomplished by chromatography or high or ultra-high-vacuum distillation.

The products prepared according to the invention are employed in natural and synthetic rubber compositions and blends of known and novel formulation, in amounts consistent with those previously employed for other silane coupling agents for the use in sulfur-vulcanizable, silica-reinforced tire rubber compositions. Exemplary of suitable amounts will be at least 2 parts per hundred parts rubber (PHR) and, preferably from about 4 to about 20 PHR, e.g., 6 to 12 PHR. The amount will also be related to the amount of silica employed, preferably the ratio by weight of silica to silane being in the range of from 4:1 to about 40:1, more narrowly from about 6:1 to about 10:1. Molar ratios of added sulfur for vulcanization to sulfur in the silane can be varied within the range of from above 0 to about 100:1 or more, preferably from 2:1 to 20:1, more narrowly from 5:1 to 10:1. The required amount of silane will decrease as its relative sulfur content increases.

Exemplary of suitable rubber compositions are sulfur-vulcanizable synthetic rubber compositions. Representative examples of suitable rubber polymers include solution styrene-butadiene rubber (SSBR), styrene-butadiene rubber (SBR), natural rubber (NR), polybutadiene (BR), ethylene-propylene co- and ter-polymers (EP, EPDM), and acrylonitrile-butadiene rubber (NBR). The rubber composition preferably is comprised of at least one diene-based elastomer, or rubber. Suitable conjugated dienes are isoprene and 1,3-butadiene and suitable vinyl aromatic compounds are styrene and alpha methyl styrene. Thus, the rubber is a sulfur curable rubber. Such diene based elastomer, or rubber, may be selected, for example, from at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35–50 percent vinyl), high vinyl polybutadiene rubber (50–75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (E-SBR) might be used having a relatively conventional styrene content of 20 to 28 percent bound styrene or, for some applications, an E-SBR having a medium to relatively high bound styrene content, namely, a bound styrene content of 30 to 45 percent. Emulsion polymerization prepared styrene/butadiene/acrylonitrile terpolymer rubbers containing 2 to 40 weight percent bound acrylonitrile in the terpolymer are also contemplated as diene based rubbers for use in this invention.

See any of U.S. Pat. Nos. 3,451,458, 5,110,969, 5,227,425 and 5,753,732, for examples of rubber compounds that can be improved with the invention with silica as a reinforcing agent. The disclosures of these patents are incorporated by reference in their entireties.

The rubber compositions, in addition to at least one elastomer of synthetic or natural origin, will contain a mineral filler, particularly silica, in amounts effective for reinforcing the rubber in its vulcanized state. The silica can be of the types known, for example described in U.S. Pat. Nos. 4,704,414, 5,227,425 and 5,753,732, and will be employed in amounts suitable for reinforcing tires, especially those having low rolling resistance. The silica will be employed at a level of from about 5 to about 100 parts per hundred parts of rubber, preferably at least 30 parts silica. Higher or lesser amounts can be employed where appropriate.

Precipitated silicas are preferred fillers. The silica may be characterized by having a BET surface area, as measured using nitrogen gas, preferably in the range of 40 to 600, and more usually in a range of 50 to 300 $m^2/g$. The silica typically may also be characterized by having a dibutylphthalate (DBP) absorption value in a range of 100 to 350, and more usually 150 to 300. Further, the silica, as well as the aforesaid alumina and aluminosilicate, may be expected to have a CTAB surface area in a range of 100 to 220. The average mercury porosity specific surface area for the silica should be in a range of 100 to 300 $m^2/g$.

The rubber composition may be compounded by methods known in the rubber compounding art, such as mixing the various sulfur-vulcanizable constituent rubbers with various commonly used additive materials such as, for example, curing aids, such as sulfur, activators, retarders and accelerators, processing additives, such as oils, resins including tackifying resins, silicas, plasticizers, fillers, pigments, fatty acid, zinc oxide, waxes, antioxidants and antiozonants, peptizing agents, and reinforcing materials such as, for example, carbon black. Depending on the intended use of the sulfur vulcanizable and sulfur vulcanized material (rubbers), the additives mentioned above are selected and commonly used in conventional amounts.

A rubber composition may prepared by a process such as by:

(A) thermomechanically mixing, in at least one preparatory mixing step, to a temperature of 140° C. to 200° C., alternatively to 140° C. to 190° C., for a total mixing time of 2 to 20, alternatively 4 to 15, minutes for such mixing step(s) (i) 100 parts by weight of at least one sulfur vulcanizable rubber selected from conjugated diene homopolymers and copolymers, and copolymers of at least one conjugated diene and aromatic vinyl compound, (ii) 5 to 100, preferably 25 to 80, phr (parts per hundred rubber) of particulate filler, wherein preferably the filler contains 1 to 85 weight percent carbon black (iii) 0.05 to 20 parts by weight filler of at least one sulfur-containing silane;

(B) subsequently blending therewith, in a final thermomechanical mixing step at a temperature to 50° C. to 130° C. for a time sufficient to blend the rubber, preferably between 1 to 30 minutes, more preferably 1 to 3 minutes, a curing agent at 0 to 5 phr; and optionally (C) curing said mixture at a temperature of 130 to 200° C. for about 5 to 60 minutes. An exemplary process for using silane coupling agents to manufacture silica containing rubber is disclosed in PCT/US98/17391, which is incorporated herein by reference.

The rubber compositions of the invention are employed to form various rubber articles, including shoe soles and tire parts, such as treads and sidewalls in the normal fashion as conventional silica-reinforced, sulfur vulcanizable rubber compositions.

Whereas the exact scope of this invention is set forth in the appended claims, the following specific examples illustrate certain aspects of the present invention and, more particularly, point out various aspects of the method for evaluating same. However, the examples are set forth for illustrative purposes only and are not to be construed as limitations on the present invention. The abbreviations g, ml, mm, m, psi, ppm, GC, MS, and NMR respectively represent gram, milliliter, millimeter, molar equivalent, pounds per square inch, parts per million, gas chromatography, mass spectrometry, and nuclear magnetic resonance spectroscopy; temperature is reported in degrees Centigrade. Unless stated otherwise, all reactions were run in standard laboratory glassware of various sizes at atmospheric pressure under an inert atmosphere of nitrogen, and all parts and percentages are by weight.

Alkoxysilane acetals were prepared by the platinum-catalyzed hydrosilations of acrolein dimethyl acetal, acrolein 1,2-propylene acetal, and methacrolein dimethyl acetal with trimethoxysilane or methyldimethoxysilane.

EXAMPLE 1

Preparation of 2-(2-Trimethoxysilylethyl)-1,3-dithiolane

To a 250 ml three-necked flask fitted with a mechanical stirrer and a distillation head were added 73.6 g of 95.2% (3,3-dimethoxypropyl)trimethoxysilane (70.07 g, 0.313 m), 32.4 g (0.344 m) of ethane-1,2-dithiol, and 0.2 g of anhydrous zinc chloride catalyst. The reaction was heated to 130° under nitrogen and maintained at that temperature for 1.75 hours, during which time 18.7 g of 95.4% methanol (89% of theory) were distilled from the flask. The crude residue, containing 90% of the title product, was distilled to provide 55.7 g of 94.3% pure product (70.1% yield). The product was characterized by GC/MS and NMR. Similar results were obtained when 0.2 wt-% of zinc hexacyanocobaltate was used as catalyst in place of zinc chloride.

EXAMPLE 2

Reaction of (3,3-Dimethocypropyl)trimethoxysilane with Ethane-1,2-dithiol using Lanthanum/Chloride The procedure and apparatus of Example 1 were used with 77.2 g (0.345 m) of (3,3-dimethoxypropyl)trimethoxysilane, 37.5 g (0.371 m) of ethane-1,2-dithiol and 0.23 g of lanthanum chloride as catalyst. After distillation of methanol, the crude product (89.6 g) contained 20% of methanol and raw materials, plus 14.5% of 2-(2-trimethoxysilylethyl)-1,3-dithiolane, 37.3% of the monosubstitution product, $(MeO)_3Si(CH_2)_2CH(OMe)S(CH_2)_2SH$, and 19.6% of a dimeric product, $[(MeO)_3Si(CH_2)_2CH(OMe)SCH_2]_2$, as determined by GC/MS.

EXAMPLE 3

Preparation of 2-(2-Methyldimethoxysilylethyl)-1,3-dithiolane

The procedure and apparatus of Example 1 were used with 36.2 g (0.177 m) of (3,3-dimethoxypropyl)methyldimethoxysilane, 18.31 g (0.195 m) of ethane-1,2-dithiol, and 0.13 g of zinc chloride catalyst. Reaction and work-up as in Example 1 provided crude product containing lesser amounts of raw materials and 69.4% of the title compound, as determined by GC/MS.

EXAMPLE 4

Preparation of 2-(2-Trimethoxysilylethyl)-1,3-Dithiane

The procedure and apparatus of Example 1 were used with 22.4 g (0.207 m) of propane-1,3-dithiol, 46.4 g (0.207 m) of (3,3-dimethoxypropyl)trimethoxysilane, 0.14 g of p-toluenesulfonic acid, and 100 ml of xylenes solvent. Methanol was removed by distillation as the contents of the flask were heated at reflux (143°) for 2 hours. The crude product, excluding solvent, contained 75% of the title product and 7.4% of the monosubstituted product, $(MeO)_3Si(CH_2)_2CH(OMe)S(CH_2)_3SH$, as determined by GC/MS.

EXAMPLE 5

Preparation of 2-(1-Methyl-2-trimethoxysilylethyl)-1,3-dithiolane

The procedure and apparatus of Example 1 were used with 25.0 g (0.102 m) of (3,3-dimethoxy-2-methylpropyl) trimethoxysilane (boiling point, 125°/25 mm, prepared by the hydrosilation of methacrolein dimethyl acetal with trimethoxysilane, as characterized by GC/MS and NMR), 9.6 g (0.102 m) of ethane-1,2-dithiol, and 0.07 g of anhydrous zinc chloride catalyst. The crude product, after distillation to a pot temperature of 195°, was 27.1 g, containing 64.3% of the title product as determined by GC/MS.

EXAMPLE 6

Hydrogenolysis of a Dithiolane

Into a 300 ml rocking autoclave were charged 58.2 g (0.331 m) of 2-(n-pentyl)-1,3-dithiolane, 1.06 g of sulfur, 0.12 g of p-toluenesulfonic acid, and 1.87 g of cobalt polysulfide catalyst (added as a 43% slurry in toluene). The autoclave was pressurized with hydrogen and maintained between 1600 and 2200 psi while being heated to 250°. After cooling and venting, the crude product contained 57% of the hydrogenolysis product, $CH_3(CH_2)_5S(CH_2)_2SH$, as determined by GC/MS. When this procedure is applied to the product of Example 1, the hydrogenolysis product, $(MeO)_3Si(CH_2)_3S(CH_2)_2SH$, is obtained.

EXAMPLE 7

Reaction of Alkoxysilane Acetal with H2S

An apparatus was assembled consisting of a 500 ml three-necked flask fitted with a mechanical stirrer, distillation head and receiver, sparge tube to introduce hydrogen sulfide, and a sodium methylate scrubber to remove hydrogen sulfide from the exiting gases. To the flask were charged 108.3 g (0.426 m) of (3,3-dimethoxypropyl)-trimethoxysilane, 0.3 g of p-toluenesulfonic acid, and 200 g of toluene solvent. The flask and contents were heated at 100–120° for 9 hours while hydrogen sulfide was introduced at 0.04 liters/minute. The flask contents were heated to 140° and volatiles (including 3-mercaptopropyltrimethoxysilane) removed at 1 mm vacuum. The crude product contained several components, including 4.3% of $[(MeO)_3SiCH_2CH=CH]_2S$ and 30.5% of cis/trans-$(MeO)_3Si(CH_2)_2CH(OMe)SCH=CHCH_2Si(OMe)_3$ as determined by GC/MS.

EXAMPLE 8

Reaction of 3-Mercaptopropyltrimethoxysilane with (3,3-Dimethoxypropyl)trimethoxysilane The procedure and apparatus of Example 1 were used with 98.1 g (0.50 m) of 3-mercaptopropyltrimethoxysilane, 52.5 g (0.227 m) of (3,3-dimethoxypropyl)-trimethoxysilane, and 0.75 g of zinc chloride catalyst. The reactants were heated at 135° C. for 2.75 hours and 11.8 g (93.3% methanol) of volatiles were removed. The crude product, 129 g, was analyzed by GC/MS and contained 27.3% 3-mercaptopropyl-trimethoxysilane, 35% cis/trans-$(MeO)_3Si(CH_2)_3S—CH=CHCH_2Si(OMe)_3$, and 12% of the dithioacetal $[(MeO)_3Si(CH_2)_3S]_2CH(CH_2)_2Si(OMe)_3$, as determined by GC/MS.

EXAMPLE 9

Preparation of 3-Mercaptopropyltrimethoxysilane and a Trithiane from an Alkoxysilane Acetal and Sulfur A series of experiments was conducted using a 300 ml rocking autoclave, charged with varying amounts of (3,3- dimethoxypropyl)trimethoxysilane (42.6–195 g), sulfur (1.05–1.2 m), cobalt or nickel polysulfide catalyst (2.5 wt-%), acetic acid or p-toluenesulfonic acid (0.5 wt-% or 0.2 wt-%, respectively), and hydrogen (1600 psi), with heat applied at 150–250° for 4–23 hours. Triethylamine and tributylamine at 0.5 wt-% were also screened in place of the acid component. Good results were obtained, for example, when run with 42.6 g of acetal, 1.05 m of sulfur, acetic acid, and cobalt polysulfide, wherein the yield of 3-mercaptopropyltrimethoxysilane, as determined by GC/MS of the crude product, was 29%. The major product, of several higher boiling components, has been assigned the trithiane structure, $[(MeO)_3Si(CH_2)_2CHS]_3$, based on spectral comparisons to a more volatile model compound.

EXAMPLE 10

Preparation of 3-Mercaptopropyltrimethoxysilane and a Trithiane from an Alkoxysilane Acetal and Hydrogen Sulfide Certain of the experiments of Example 9 were repeated using hydrogen sulfide rather than sulfur as the source of sulfur. Good results were obtained when run with 121.5 g of the alkoxysilane acetal, 0.5 wt-% of acetic acid, 2.5 wt-% of cobalt polysulfide catalyst, 34g (1.85 m) of hydrogen sulfide, and hydrogen at 1600 psi as charged at room temperature. Heating up to 200° and holding for 2.25 hours provided 158.3 g of crude product from which a 61% yield of 3-mercaptopropyltrimethoxysilane (based on acetal) was recovered by distillation. Nondistilled product was largely the same trithiane as observed in Example 9.

The above description is intended to enable the person skilled in the art to practice the invention. It is not intended to detail all of the possible modifications and variations which will become apparent to the skilled worker upon reading the description. It is intended, however, that all such modifications and variations be included within the scope of the invention which is defined by the following claims. The claims are meant to cover the indicated elements and steps in any arrangement or sequence which is effective to meet the objectives intended for the invention, unless the context specifically indicates the contrary.

What is claimed is:

1. A method for preparing a sulfur silane comprising reacting an alkoxysilane acetal with a sulfurating agent in the presence of a catalyst.

2. The method of claim 1 wherein said sulfur-containing silane has the formula $[R^1_x(R^2O)_{3-x}SiRCR^3(Y)_jS]_n(X)_j$ where R is a saturated or unsaturated linear, branched, or cyclic divalent hydrocarbon group of 2 to 12 carbon atoms optionally containing divalent —O— or —S— linkages; $R^1$ is an alkyl group of 1 to 4 carbon atoms, an aryl group of 6 to 12 carbon atoms, or an aralkyl or alkaryl group of 7 to 13 carbon atoms; each $R^2$ can be $R^1$ or the 2 $R^2$ groups taken together form an R group so as to form a ring; $R^3$ is a hydrogen atom or $R^1$; $R^4$ is $R^3$, —RSH, or —RSiR$^1_x$(OR$^2$)$_{3-x}$; x is an integer having a value of 0, 1, or 2, n is an integer having a value of 1 to 4; j=0 or 1, when n=1, j=1, when n>1, j=0, X is $R^4$ and Y is —SR$^4$ or —OR$^2$, or alternatively X and Y taken together are —SR— which forms a 1,3-dithiacycloalkane ring with the carbon bearing $R^3$ when n=1, or X and Y are both hydrogen atoms when n=1 and $R^4$ is a hydrogen atom.

3. The method of claim 2 wherein R is a saturated linear or branched divalent hydrocarbon group of 2 or 3 carbon atoms; $R^1$ is a methyl group; $R^2$ is $R^1$, an ethyl group, or 2 $R^2$ groups taken together form an R group; $R^3$ is a hydrogen atom or a methyl group; $R^4$ is a hydrogen atom, the group —RSH, or the group —RSiR$^1_x$(OR$^2$)$_{3-x}$; and x is an integer having a value of 0 or 1; n is an integer having a value of 1 or 3.

4. The method of claim 2 wherein said alkoxysilane acetal is selected from the group consisting of $(MeO)_3SiCH_2CH_2CH(OMe)_2$, $Me(MeO)_2SiCH_2CH_2CH(OMe)_2$, $(MeO)_3SiCH_2CHMeCH(OMe)_2$, $Me(MeO)_2SiCH_2CHMeCH(OMe)_2$, $(EtO)_3SiCH_2CH_2CH(OMe)_2$, $Me(EtO)_2SiCH_2CH_2CH(OMe)_2$, $(EtO)_3SiCH_2CH_2CH_2(OEt)_2$, and $Me(EtO)_2SiCH_2CH_2CH(OEt)_2$, and said sulfurating agent is selected from the group of hydrogen sulfide, HSRSH and HSRSiR$^1_x$(OR$^2$)$_{3-x}$ and sulfur.

5. The method of claim 1 wherein the catalyst is selected from the group of Bronsted acids and Lewis acids in liquid or solid form and is at a concentration of 0.05 to 5 wt-% of the combined reactants.

6. The method of claim 1 wherein the sulfurating agent is hydrogen sulfide or sulfur in the presence of hydrogen gas and a reduction catalyst and the major product is HSRSiR$^1_x$(OR$^2$)$_{3-x}$ where R is a saturated linear or branched divalent hydrocarbon group, $R^1$ is a methyl group, $R^2$ is a methyl group or an ethyl group, and x is an integer having a value of 0 or 1.

7. The method of claim 6 wherein the reduction catalyst is cobalt polysulfide and the major product is $HS(CH_2)_3Si(OMe)_3$.

8. The method according to claim 7 additionally comprising the step of removing alcohol from the sulfur silane following the reaction.

9. A silane selected from the group consisting of:

$[R^1_x(R^2O)_{3-x}SiRC(R^3)(OR^2)S]_2R$;

$R^1_x(R^2O)_{3-x}SiRC(R^3)_2SRSH$;

$[R^1_x(R^2O)_{3-x}SiRCR^3S]q$ wherein $q \geq 2$; and $R^1_x(R^2O)_{3-x}SiR$-cyclo$(C(R^3)SRS)$;

wherein:
R is a saturated or unsaturated linear, branched, or cyclic divalent hydrocarbon group of 2 to 12 carbon atoms optionally containing divalent —O— or —S— linkages; $R^1$ is an alkyl group of 1 to 4 carbon atoms, an aryl group of 6 to 12 carbon atoms, or an aralkyl or alkaryl group of 7 to 13 carbon atoms; each $R^2$ can be $R^1$ or the 2 $R^2$ groups taken together form an R group so as to form a ring; $R_3$ is a hydrogen atom or $R^1$; and x is an integer having a value of 0, 1, or 2.

10. A silane according to claim 9 of the formula $[R^1_x(R^2O)_{3-x}SiRC(R^3)(OR^2)S]_2R$.

11. A silane according to claim 9 of the formula $R^1_x(R^2O)_{3-x}SiRC(R^3)_2SRSH$.

12. A silane according to claim 9 of the formula $[R^1_x(R^2O)_{3-x}SiRCR^3]_q$ wherein $q \geq 2$.

13. A silane according to claim 9 of the formula $R^1_x(R^2O)_{3-x}SiR$-cyclo$(C(R^3)SRS$—$)$.

14. A silane according to claim 9 selected from the group consisting of

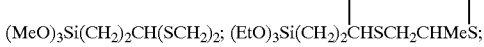
$(MeO)_3Si(CH_2)_2CH(SCH_2)_2$; $(EtO)_3Si(CH_2)_2CHSCH_2CHMeS$;

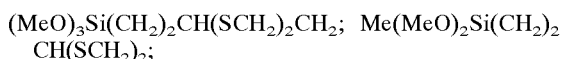
$(MeO)_3Si(CH_2)_2CH(SCH_2)_2CH_2$; $Me(MeO)_2Si(CH_2)_2CH(SCH_2)_2$;

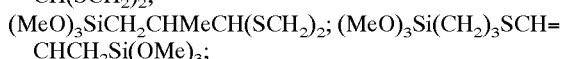
$(MeO)_3SiCH_2CHMeCH(SCH_2)_2$; $(MeO)_3Si(CH_2)_3SCH=CHCH_2Si(OMe)_3$;

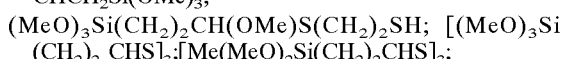
$(MeO)_3Si(CH_2)_2CH(OMe)S(CH_2)_2SH$; $[(MeO)_3Si(CH_2)_2CHS]_3$;$[Me(MeO)_2Si(CH_2)_2CHS]_3$;

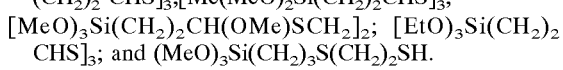
$[MeO)_3Si(CH_2)_2CH(OMe)SCH_2]_2$; $[(EtO)_3Si(CH_2)_2CHS]_3$; and $(MeO)_3Si(CH_2)_3S(CH_2)_2SH$.

15. A rubber composition comprising rubber, silica and a silane of claim 9.

* * * * *